United States Patent
Sham

(10) Patent No.: US 10,085,683 B1
(45) Date of Patent: Oct. 2, 2018

(54) VEHICLE FATIGUE MONITORING SYSTEM

(71) Applicant: Wellen Sham, Taipei (TW)

(72) Inventor: Wellen Sham, Taipei (TW)

(73) Assignee: Wellen Sham, Taipei (TW)

( * ) Notice: Subject to any disclaimer, the term of this patent is extended or adjusted under 35 U.S.C. 154(b) by 0 days.

(21) Appl. No.: 15/675,142

(22) Filed: Aug. 11, 2017

(51) Int. Cl.
| | |
|---|---|
| *G08B 23/00* | (2006.01) |
| *A61B 5/18* | (2006.01) |
| *G02B 27/00* | (2006.01) |
| *B60K 28/06* | (2006.01) |
| *G06Q 50/30* | (2012.01) |
| *G08G 1/01* | (2006.01) |
| *G06K 9/00* | (2006.01) |
| *B60W 40/08* | (2012.01) |

(52) U.S. Cl.
CPC ............... *A61B 5/18* (2013.01); *B60K 28/06* (2013.01); *B60W 40/08* (2013.01); *G02B 27/0093* (2013.01); *G06K 9/00228* (2013.01); *G06Q 50/30* (2013.01); *G08G 1/0112* (2013.01); *B60W 2040/0818* (2013.01)

(58) Field of Classification Search
CPC ......... A61B 5/18; B60K 28/06; B60W 40/08; G02B 27/0093; G06K 9/00228; G06Q 50/30; G08G 1/0112
USPC ........................................................ 340/576
See application file for complete search history.

(56) References Cited

U.S. PATENT DOCUMENTS

| | | | |
|---|---|---|---|
| 6,661,345 B1 | 12/2003 | Bevan et al. | |
| 7,509,212 B2 | 3/2009 | Bodin et al. | |
| 7,666,151 B2 | 2/2010 | Sullivan et al. | |
| 8,140,358 B1 | 3/2012 | Ling et al. | |
| 8,311,858 B2 | 11/2012 | Everett et al. | |
| 8,359,901 B2 | 1/2013 | Freund et al. | |
| 8,761,821 B2 | 6/2014 | Tibbitts et al. | |
| 8,787,936 B2 | 7/2014 | Tibbitts et al. | |
| 8,892,451 B2 | 11/2014 | Everett et al. | |
| 8,924,240 B2 | 12/2014 | Depura et al. | |
| 9,053,516 B2 | 6/2015 | Stempora | |

(Continued)

FOREIGN PATENT DOCUMENTS

DE    10 2015 105581 A1    5/2016

OTHER PUBLICATIONS

Pogue, David, iPhone: The Missing Manual, Nov. 17, 2014, O'Reilly Media, 8th Edition, Chapter 2 and Chapter 4, 34 pages. Retrieved from http://techbus.safaribooksonline.com/print?xmlid=9781491947982%Fch01.

(Continued)

*Primary Examiner* — Kerri McNally
(74) *Attorney, Agent, or Firm* — Kilpatrick Townsend & Stockton LLP

(57) ABSTRACT

Embodiments can provide a real-time fatigue monitoring system for detecting and/or monitoring a fatigue condition of a driver of a driving apparatus. In some embodiments, the fatigue monitoring system can include a set of one or more sensors for detecting a physiological condition of the driver, a head movement detection device, one or more processing devices, and/or any other components. In some embodiments, the fatigue condition detection system may include a processing device configured to determine occurrence of a fatigue condition in response to the detection of a physiological condition of the driver is below a threshold while the driver's head movement is tilting downwards.

16 Claims, 7 Drawing Sheets

(56) References Cited

U.S. PATENT DOCUMENTS

| | | |
|---|---|---|
| 9,094,816 B2 | 7/2015 | Maier et al. |
| 9,141,975 B2 | 9/2015 | Meller |
| 9,162,753 B1 | 10/2015 | Panto et al. |
| 9,440,657 B1 * | 9/2016 | Fields ................ B60K 28/066 |
| 9,460,601 B2 | 10/2016 | Mimar |
| 9,694,771 B1 | 7/2017 | Ding |
| 9,809,169 B1 | 11/2017 | Naboulsi |
| 2003/0204290 A1 | 10/2003 | Sadler et al. |
| 2006/0167597 A1 | 7/2006 | Bodin et al. |
| 2006/0212195 A1 | 9/2006 | Veith et al. |
| 2008/0074307 A1 | 3/2008 | Boric-Lubecke et al. |
| 2008/0163670 A1 | 7/2008 | Georgeson |
| 2008/0191863 A1 | 8/2008 | Boling et al. |
| 2009/0293589 A1 | 12/2009 | Freund et al. |
| 2010/0134627 A1 | 6/2010 | Yen et al. |
| 2010/0222976 A1 | 9/2010 | Haug |
| 2011/0090047 A1 | 4/2011 | Patel |
| 2011/0307123 A1 | 12/2011 | Abe et al. |
| 2012/0303392 A1 | 11/2012 | Depura et al. |
| 2013/0027208 A1 * | 1/2013 | Tao ................ G08B 21/06 340/575 |
| 2013/0070043 A1 | 3/2013 | Geva et al. |
| 2013/0204153 A1 | 8/2013 | Buzhardt |
| 2013/0297099 A1 | 11/2013 | Rovik |
| 2014/0039934 A1 | 2/2014 | Rivera |
| 2014/0089101 A1 | 3/2014 | Meller |
| 2014/0293053 A1 | 10/2014 | Chuang |
| 2014/0309864 A1 | 10/2014 | Ricci |
| 2015/0019266 A1 | 1/2015 | Stempora |
| 2015/0025917 A1 | 1/2015 | Stempora |
| 2015/0127215 A1 | 5/2015 | Chatterjee |
| 2015/0140954 A1 | 5/2015 | Maier et al. |
| 2015/0160019 A1 | 6/2015 | Biswal et al. |
| 2015/0197205 A1 | 7/2015 | Xiong et al. |
| 2015/0263886 A1 | 9/2015 | Wang et al. |
| 2015/0328985 A1 | 11/2015 | Kim et al. |
| 2015/0334545 A1 | 11/2015 | Maier et al. |
| 2016/0001781 A1 * | 1/2016 | Fung ................ G06F 19/345 701/36 |
| 2016/0042637 A1 | 2/2016 | Cahill |
| 2016/0180144 A1 | 6/2016 | Tatourian et al. |
| 2016/0272214 A1 | 9/2016 | Sham |
| 2016/0330601 A1 | 11/2016 | Srivastava |
| 2017/0011562 A1 | 1/2017 | Hodges |
| 2017/0174158 A1 | 6/2017 | Ding |
| 2017/0305349 A1 | 10/2017 | Naboulsi |
| 2017/0355377 A1 | 12/2017 | Vijaya Kumar et al. |
| 2018/0000397 A1 | 1/2018 | Sham |

OTHER PUBLICATIONS

U.S. Appl. No. 14/977,627, filed Dec. 21, 2015 Non-Final Rejection dated Apr. 7, 2016, all pages.

U.S. Appl. No. 14/977,627, filed Dec. 21, 2015 Final Rejection dated Oct. 20, 2016, all pages.

U.S. Appl. No. 14/977,627, filed Dec. 21, 2015 Notice of Allowance dated Feb. 28, 2017, all pages.

U.S. Appl. No. 15/199,268, filed Jun. 30, 2016 Non-Final Rejection dated Nov. 9, 2016, all pages.

U.S. Appl. No. 15/199,268, filed Jun. 30, 2016 Final Rejection dated Jun. 8, 2017, all pages.

U.S. Appl. No. 62/272,706, filed Dec. 30, 2015, Inventor: Wellen Sham.

European Search Report for EP17179153 dated Oct. 19, 2017, all pages.

U.S. Appl. No. 15/675,108, filed Aug. 11, 2017 Non-Final Rejection dated Nov. 30, 2017, all pages.

Droitcour et al, "Signal-to-Noise Ratio in Doppler Radar System for Heart and Respiratory Rate Measurements." IEEE Transactions on Microwave Theory and Techniques, vol. 57, No. 10, Oct. 2009, 10 pages.

Lu et al., "A New Stochastic Model to Interpret Heart Rate Variability." Proceedings on the 25th Annual International Conference of the IEEE EMBS. Sep. 17-21, 2003.

U.S. Appl. No. 15/199,268, filed Jun. 30, 2016 Non-Final Rejection dated Feb. 20, 2018, all pages.

* cited by examiner

400

VEHICLE FATIGUE MONITORING SYSTEM

CROSS-REFERENCES TO RELATED APPLICATIONS

The present disclosure relates to the following applications: U.S. Nonprovisional application Ser. No. 15/199,268, filed Jun. 30, 2016; U.S. Nonprovisional application Ser. No. 14/977,627, filed Dec. 21, 2015; and U.S. Nonprovisional application Ser. No. 15/063,435, filed Mar. 7, 2016. The entire contents of each of these applications are incorporated by reference herein for all purposes.

BACKGROUND OF THE INVENTION

The present disclosure relates to vehicle monitoring technology, and more particularly to methods for increasing vehicle safety by monitoring a vehicle whose operator has been detected to have a fatigue condition.

A driver's fatigue condition could lead to unsafe driving. When driving fatigued, a driver may lose his/her consciousness temporarily and drive erratically to cause a havoc on the road. The risk is obvious when someone is fatigued at the wheel. The National Transportation Safety Board (NTSB) in the United States has indicated the significant danger of fatigued drivers operating heavy vehicles. 52% of heavy truck single vehicle accidents were fatigue-related. Annually, it is estimated there are 40,000 injuries and 1,550 fatalities caused from fatigued persons at the wheel. Drivers who are fatigued have delayed reactions and make bad decisions. Not only are they putting themselves in danger, but they are a risk to everyone else on the road.

Accordingly, there is a need to have a driving apparatus that are equipped to detect a fatigue condition of a driver while driving, and to notify relevant entities to address risks associated the detected fatigue condition of the driver.

BRIEF SUMMARY OF THE INVENTION

Embodiments can provide a real-time fatigue monitoring system for detecting and/or monitoring a fatigue condition of a driver of a driving apparatus. In some embodiments, the fatigue monitoring system in accordance with the disclosure can include a set of one or more sensors for detecting a physiological condition of the driver, a head movement detection device, one or more processing devices, and/or any other components. The sensor(s) can be configured to collect real-time physiological data about the driver, such as electrocardiogram (EKG), heart rate, and blood level data, and transfers the physiological data to a first processing device. In some embodiments, the sensor(s) may include an electrocardiogram detection component configured to detect a cardiac activity of the driver. In some embodiments, the electrocardiogram detection component may be configured to generate EKG signal indicating a cardiac activity of the driver. The first processing device in those embodiments may be configured to extract various EKG data, for example, the P wave, Q wave, R wave, S wave, T wave and/or any other EKG data from the EKG signal. In some embodiments, the sensor(s) may include a heart rate monitoring device configured to detect a heart rate of the driver. In some embodiments, the sensor(s) may include a blood level detection component configured to detect a blood level of the driver. The first processing device may be configured to compare the physiological data received from the sensor(s) with one or more thresholds and determine if any of the thresholds have been breached. For example, the first processing device may be configured to compare the detected heart rate of the driver with a preset heart rate threshold (e.g., 60 beats per minute) to determine if the heart rate of the driver has dropped below that threshold.

The head movement detection device can be configured to collect information about head positions of the driver. In some embodiments, the head movement detection device may include a camera component configured to capture images of the driver periodically or non-periodically. In some embodiments, the head movement detection device may include a motion sensing component configured to acquire motion information regarding a movement of the head of the driver. The images and/or motion data captured by the head motion detection device can be transferred to a second processing device. The second processing device can be configured to determine a movement of the head of the driver. For example, the second processing device can be configured to determine a direction of the movement of the driver's head, a distance of the head movement, a velocity of the head movement, an orientation change of the head movement, and/or any other aspects of the driver's head movement.

In some embodiments, the fatigue condition detection system in accordance with the disclosure may include a third processing device. The third processing device may be configured to determine occurrence of a fatigue condition in response to the detection of a physiological condition of the driver is below a threshold while the driver's head movement is tilting downwards. For example, the third processing device may be configured to examine the head movement of the driver when the driver's heart rate is detected as being below 60 beat/minute. In that example, the third processing device can be configured to determine a velocity and direction of the driver's head in the last 3 seconds and monitor the driver's head movement for another 3 seconds. If the movement of the driver's head within those six seconds indicates the driver's head is tilting downwards with a velocity within a predetermined range, the third processing device may determine the occurrence of a fatigue condition of the driver has been detected for the driver.

In some embodiments, one or more of the first, second and third processing devices may be a same processing device. In some embodiments, one or more of the first, second, and third processing devices may be arranged within a driving apparatus which the driver is operating. In some embodiments, one or more of the first, second, and third processing devices may be arranged remotely in a processing center and configured to detect the fatigue condition of the driver as a cloud service.

This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings, and each claim.

The foregoing, together with other features and embodiments, will become more apparent upon referring to the following specification, claims, and accompanying drawings.

DETAILED DESCRIPTION OF THE INVENTION

Figure 1:
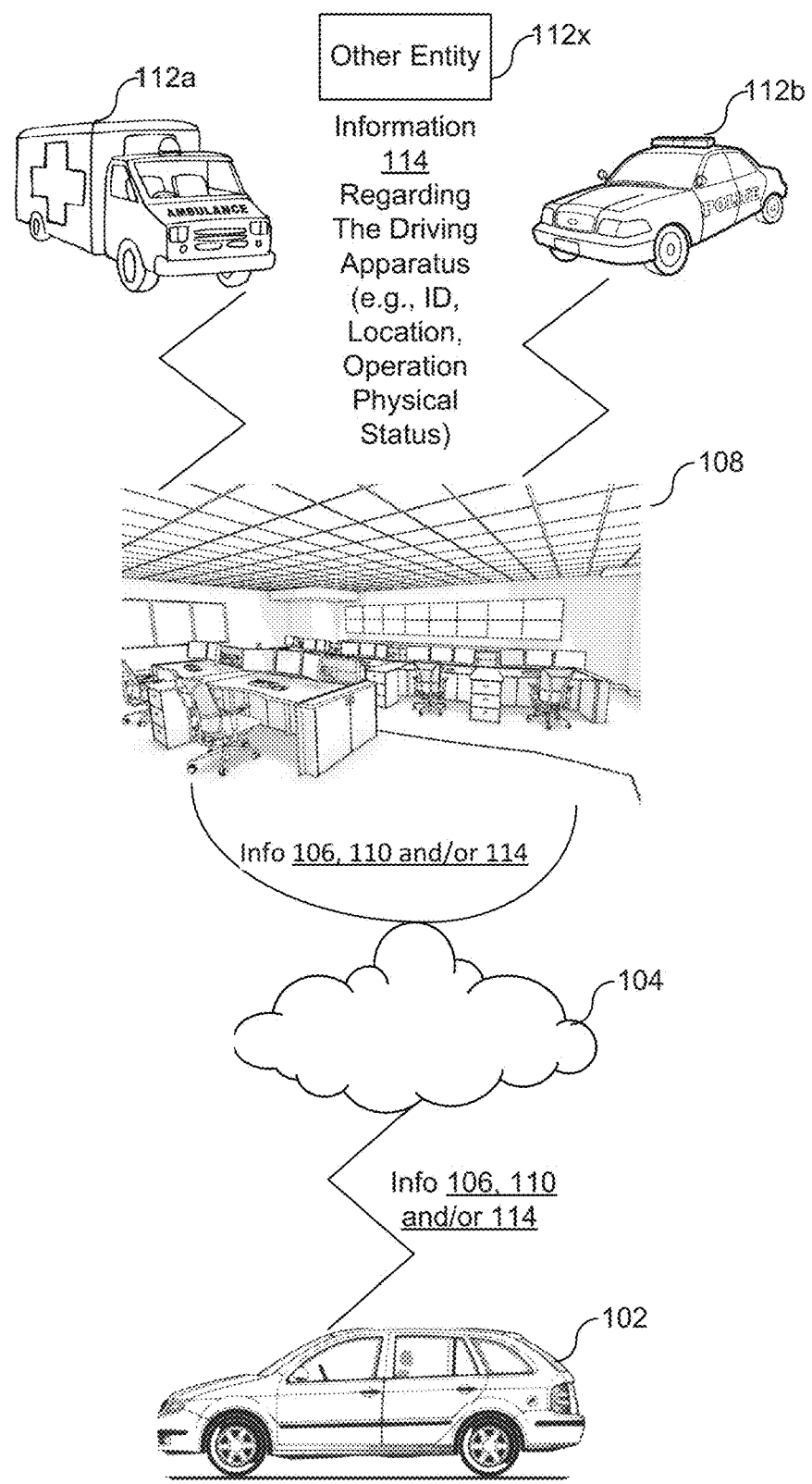
FIG. 1 generally illustrates an infrastructure for detecting a fatigue condition of an operator of a driving apparatus to improve safety in accordance with the disclosure.

Various technologies can be used to try to detect driver drowsiness. For example, certain systems have been developed to collect steering inputs of a driver and determining a steering pattern of the driver. Those systems typically involve calculations of steering movements by the driver and typically require software for such to be equipped in the vehicle. Certain systems have been developed to monitor vehicle positioning in the lane and determine if the driver is engaging in an erratic driving due to fatigue when the vehicle is detected to be swerving in the lane or between lanes. These systems typically require a sophisticated lane monitoring system and are prone to mistakes when there is no clear lane indication in the road (e.g., in certain rural areas). Certain systems have been developed to track eyelid movement to determine whether the driver is drowsy. These systems typically require an image capturing system positioned to capture the eyes of the driver very precisely and sophisticated software configured to analyze different eye movements that may be potentially engaged in by the driver.

The inventors had an insight into detecting a fatigue condition of a driver simply by comparing a physiological condition of the driver (e.g., a heart rate of the driver) and a head movement of the driver. The physiological condition may be an indicia condition indicating the driver is drowsy or fatigued, such as the heart rate, cardiac activities, blood level or any other fatigue indicia condition. Such a condition is typically easy to detect and a simple threshold may be preset for indicating that the driver may be fatigued. For example, a simple heart rate threshold may be set such that when the driver's heart rate drops below the threshold (e.g., 60 beats per minute), it can be indicated that the driver may be fatigued. Such a comparison can avoid some of the complicated pattern calculations required by the prior art drowsiness detection technologies mentioned above and can be relatively cheaply implemented.

However, the inventors also had an insight that simply relying on a physiological condition of the driver to detect whether the driver is fatigued may not be reliable. For addressing this issue, a detection of a head movement of the driver can be used. Typically, fatigue of the driver involves eyelid movement accompanying by a head movement as well as extraocular muscles movement. Measurement of head movement can be performed by using an instrument, such as a camera or motion capture system positioned to capture the head of driver. Unlike the camera or cameras for detecting eyelid movements of the driver, such a head movement capturing instrument need not be positioned very precisely to capture a movement of the eyes of the driver. Rather, head movement capturing device can be positioned to capture generally the movement of the head and thus less susceptible to mistakes.

The movement of the driver's head can then be examined when the physiological condition of the driver indicates that the driver may be fatigued. For example, when the heat rate, cardiac activity, blood level, and/or any other physiological condition of the driver is below a certain threshold level, the movement of the driver's head may be analyzed. For instance, if the driver's head is detected to be moving downwards at a certain velocity immediately and/or during the physiological condition below the threshold level being detected, it may be determined that the driver is fatigued and a signal indicating such may be generated.

Various specific embodiments of the present disclosure will be described below with reference to the accompanying drawings constituting a part of this specification. It should be understood that, although structural parts and components of various examples of the present disclosure are described by using terms expressing directions, e.g., "front", "back", "upper", "lower", "left", "right" and the like in the present disclosure, these terms are merely used for the purpose of convenient description and are determined on the basis of exemplary directions displayed in the accompanying drawings. Since the embodiments disclosed by the present disclosure may be set according to different directions, these terms expressing directions are merely used for describing rather than limiting. Under possible conditions, identical or similar reference numbers used in the present disclosure indicate identical components.

FIG. 1 generally illustrates an infrastructure for detecting a fatigue condition of an operator of a driving apparatus 102 to improve safety in accordance with the disclosure. The driving apparatus 102 may include any driving apparatus that moves in distance. Examples of driving apparatus 102 may include a vehicle such as a car, a bus, a train, a truck, a tram, or any other type of vehicle; may include a vessel such as a boat, a ship, a barge, a ferry or any other type of watercraft; may include an aircraft such as an airplane, a spaceship, or any other type of aircraft; or may include any other transportation apparatus. In one example, the driving apparatus 102 is an electrical automobile. As shown, the driving apparatus 102 can generate information 106 from time to time. The information 106 can include a status indicating an abnormal physiological condition ("abnormal condition status") having been detected for the operator of the driving apparatus 102, a status indicating that a particular sensing device is disconnected from the operator (a "disconnect status"), and/or any other status information regarding the operator of the driving apparatus 102. The information 106 can include identification information regarding the operator of the driving apparatus 102, and/or the apparatus 102. The abnormal condition status generated by driving apparatus 102 can indicate EKG activities of the operator are blow a threshold level, a heart rate of the operator is below a hear rate threshold, a blood level of the operator is below a threshold level, and/or any other physiological conditions of the operator of the driving apparatus having been detected.

In some embodiments, the driving apparatus 102 can generate information 110 indicating a head movement of the operator within a time window. For example, the driving apparatus 102 may include a head movement detection component configured to capture motion information regarding the operator of the driving apparatus 102 every other seconds. The information 110 generated by the driving apparatus 102 may indicate a direction, a speed, an orientation change of the driver's head movement within the time window. In some embodiments, the driving apparatus 102 can generate information 114 indicating a fatigue condition of the operator of the driving apparatus 102 is detected.

As shown, in some embodiments, the some or all of the information 106, 110 and 114 can be transmitted from driving apparatus 102 to a control center 108 via a network 104. The network 104 can employ a wireless transmission technology such as ultra high frequency radio, cellular, WIFI, bluetooth, infrad, laser, and/or any other wireless transmission technology. Information 106 can be transmitted through network 104 to the control center 108. The control center 108 can house one or more servers. The one or more servers in the control center 108 can be configured to receive information 106. The one or more servers in the control center 108 can be configured to generate a notification in response to the fatigue condition of the driver having been detected. In some embodiments, the one or more servers in the control center 108 can be configured to determine the fatigue condition of the driver has occurred based on information 106 and information 110 received from the driving apparatus 102. In certain embodiments, the one or more servers in the control center 108 can be configured to determine a risk level in response to the fatigue condition of the driver having been detected, and/or any other information. In certain embodiments, the one or more server in the control center 108 can be configured to generate notifications based on the determined risk level. The notifications can include a notification to a human operator in the control center 108, a notification to a healthcare facility 112a, a law enforcement agency 112b, an emergency contact for the operator of driving apparatus 102, an insurance agency, and/or any other entities. The notification can include identification information 114 regarding the operator and/or the driving apparatus 102.

Figure 2:
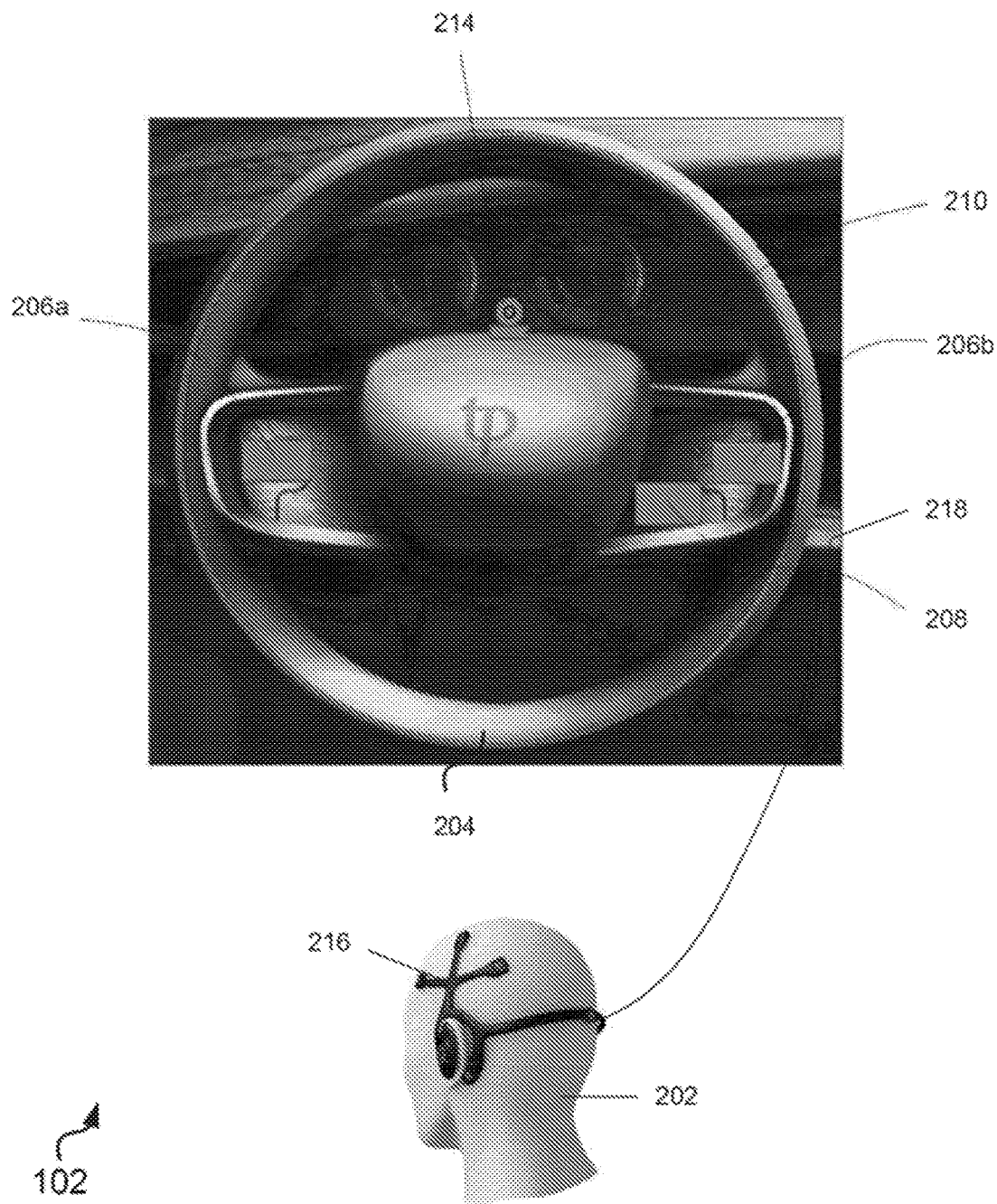
FIG. 2 illustrates some sensing devices that can be placed within driving apparatus for generating a physiological condition status.

With the infrastructure for facilitating monitoring the driving apparatus 102 to improve safety having been generally described, attention is now directed to FIG. 2. FIG. 2 illustrates some sensing devices that can be placed within driving apparatus 102 for generating a physiological condition status, and/or a disconnect status as described above. As shown, in certain embodiments, as in this embodiment, the driving apparatus 102 can be operated by an operator 202 through a steering wheel 204. The driving apparatus 102 can comprise one or more sensing devices arranged at different positions on the steering wheel 204 of the driving apparatus 102. However, the arrangement of the sensing devices in the driving apparatus 102 illustrated in FIG. 2 is not intended to be limiting. The sensing devices may be arranged at various locations throughout the driving apparatus 102 other than around the steering wheel 204. In U.S. patent application Ser. No. 62/272,706, filed Dec. 30, 2015 and entitled "METHOD FOR RECOGNIZING VEHICLE DRIVER AND DETERMINING WHETHER DRIVER CAN START VEHICLE", various sensing devices and methods thereof are provided. U.S. patent application Ser. No. 62/272,706 is incorporated by reference herein.

As shown in this example, the sensing devices may include electrocardiogram (EKG) sensing devices 206a and 206b arranged on the left side and the right side of the steering wheel 204, a heart rate detection device 208, an blood level detection device 210, and a head movement detection device 214, a EEG sensing device 216, an EEG signal processing device 218 and/or any other sensing devices.

The EKG sensing devices 206a and 206b can be configured to acquire EKG signals reflecting heart activities of operator 202. The EKG sensing devices 206a and 206b can be activated when the operator 202's hands are laid on the two sides of the steering wheel 204. The EKG signals acquired by the EKG sensing devices 206a and 206b can indicate magnitudes of heart electrical potentials of operator 202. The measured heart potentials can be recorded over a period of time, for example 10 seconds. The overall magnitude and direction of heart's electrical depolarization can then be captured and analyzed to extract different cardiac characteristics of operator 202, including P, Q, R, S and T waves.

The heart rate detection device 208 can be configured to acquire a heart rate of operator 202. The heart rate detection device 208 may detect the heart rate of operator 202 through detecting a pulse of the operator 202. A variety of existing heart rate detection technologies can be fitted in the driving apparatus 102 to detect the heart rate of the operator 202. In some embodiments, the heart rate detection device 208 may employ optics to measure heart rate using Infrared light. This can be achieved by production of infrared light by an internal bulb in the heart detection device 208. As Infrared light is absorbed by the blood, a sensor measures the amount that the infrared light is darkened. If it is significantly darker, due to the pulse causing a temporary increase in the amount of blood that is travelling through the measured area. That can be counted as a heart pulse.

The blood level detection device 210 can be configured to acquire samples of breathing exhaled by operator 202 to estimate the operator 202's blood level. In certain embodiments, a fuel cell can be arranged in or with the blood level detection device 210. In some embodiments, the fuel cell can convert alcohol in the breathing gas of the operator 202 into an electrical signal of which the quantity of electricity is directly proportional to the blood content to determine the blood level.

In some embodiment, the head movement detection device 214 can include a camera and can be configured to capture an image of operator 202's face from time to time and analyze the captured image. For example, the head movement detection device 214 can be configured to capture an image of operator 202's face once every 3 seconds. The analysis performed by head movement detection device 214 can include image recognition to identify the head area of the operator 202. It should be understood that, the camera component in the head movement detection device 214 does not have to capture images of operator 202 for determining a head movement of operator 202. In some embodiments, the head movement detection device 214 may include a motion sensor configured to detect motion of the operator's head. In those examples, the operator 202 may be asked to wear one or more markers on his/her head so that the movement of the marker can be captured by the motion sensor component of the head movement detection device 214.

The EEG device 216 can be configured to acquire signals indicating EEG activities of operator 202. As shown the EEG device 216 can be a wearable device that can be worn by operator 202 on the head. The EEG device 216 may include one or more electrodes, each of which can be connected to on input of a differential amplifier. The electrodes can acquire signals indicating electrical potentials generated by neurons of operator 202. The amplifiers can amplify the voltage to generate EEG signals indicating brain activities of operator 202. In certain embodiments, as in this example, the EEG device 216 can be operatively connected to an EEG processing device 218. In those embodiments, the EEG signals acquired by the EEG device 216 can be processed and analyzed to determine whether the EEG activities of operator 202 is abnormal.

It should be understood various devices described above are not intended to be limiting and are provided merely for illustration. In some of embodiments, one or more of those devices may be arranged in the driving apparatus 102 in manners substantially consistent with those shown in FIG. 2. However, in some embodiments, one or more of those devices may be arranged in the driving apparatus 102 in manners different from those shown in FIG. 2. For example, it is contemplated that the head movement detection device 214 may be placed on the rear windshield of the driving apparatus facing the back of the operator's head. Other examples are contemplated.

Figure 3:
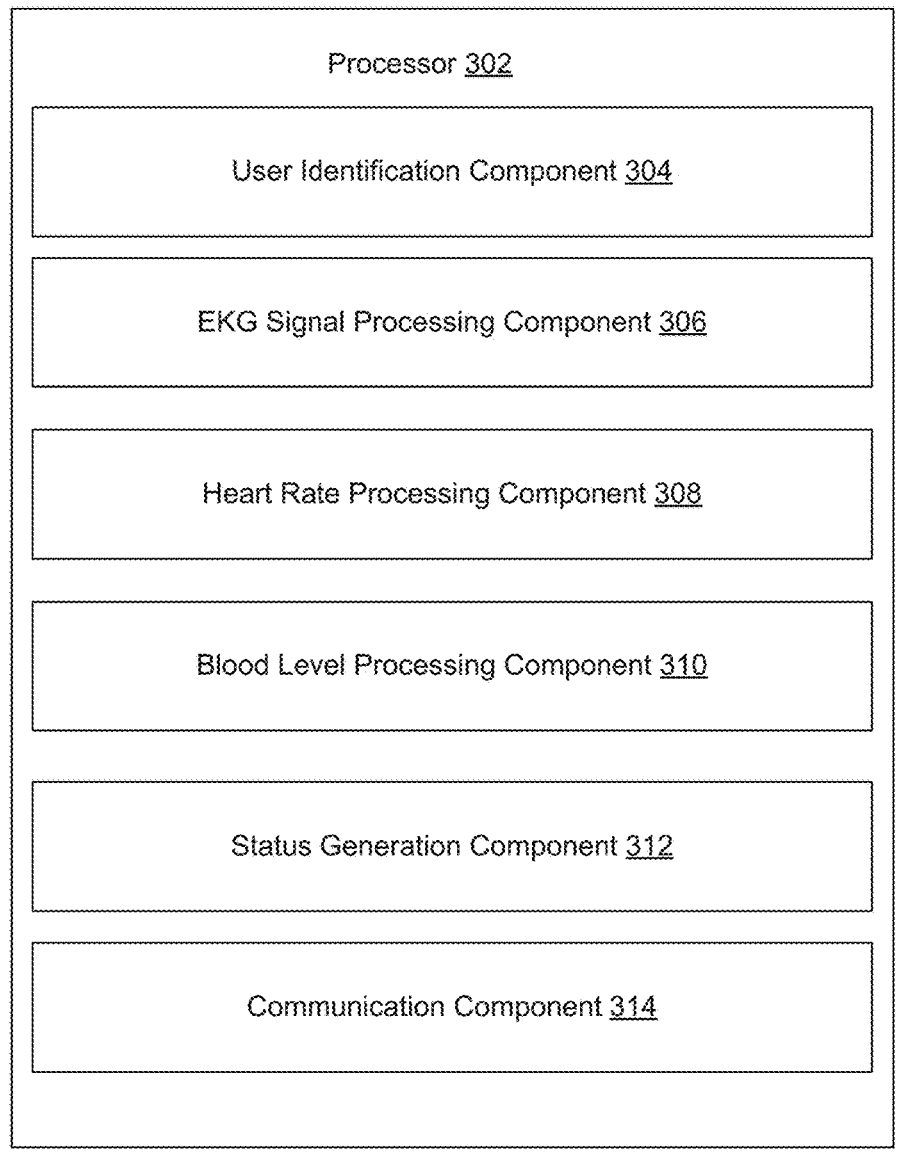
FIG. 3 illustrates an exemplary processing device configured to facilitate determining a physiological condition of an operator of driving apparatus in accordance with the disclosure.

FIG. 3 illustrates an exemplary processing device 300 configured to facilitate determining a physiological condition of an operator of driving apparatus 102 in accordance with the disclosure. As shown, the processing device 300 can include one or more of a processor 302 configured to implement computer program components. The computer program components can include a user identification component 304, an EKG signal processing component 306, a heart rate processing component 308, a blood level processing component 310, a status generation component 312, a communication component 314, and/or any other components. In some embodiments, the processing device 300 may be arranged within the driving apparatus 102. In those embodiments, the processing device 300 may be configured to communicate with various sensors and devices for detecting physiological conditions of the operator 202 described herein through short range communication methods, such as Bluetooth, WiFi and/or any short range communication methods. In some embodiments, the processing device 300 may be arranged within the control center 108, for example as a remote server provided by the control center 108. In those embodiments, the processing device 300 may be configured to communicate with the various sensors and devices for detecting physiological conditions of the operator 202 described herein through network 104.

The user identification component 304 can be configured to identify the operator 202. The identification of the operator 202 by the user identification component 304 can be made based on the fingerprint image acquired by a fingerprint detection component provided in the driving apparatus 208, the image of operator 202's face captured by the head movement detection device 214, and/or any other identification information regarding operator 202. For example, the identification by the user identification component 304 may involve analyzing features in the fingerprint image and/or in the facial image of the operator 202, and compared the obtained features with features of registered operators. Upon a match, the user identification component 304 can be configured to obtain a user ID of the identified operator 202.

The EKG signal processing component 306 can be configured to receive EKG signals generated by the EKG sensing device 206; and to analyze the EKG signals. The analysis of the EKG signals by the EKG signal processing component 306 can include acquiring the user ID determined by the user identification component 304, retrieving a predetermined EKG threshold patterns for the identified operator 202 using the user ID, comparing the EKG signals with the retrieved threshold EKG pattern, determine whether the detected EKG pattern of the operator 202 has dropped below the threshold EKG pattern and/or any other operations. In the case when the detected EKG pattern of operator 202 is determined as having dropped below the threshold EKG pattern, a control signal can be generated to instruct the status generation component 312 to generate a status accordingly.

In certain embodiments, the EKG signal processing component 306 can be configured to generate a control signal after not receiving the EKG signals from the EKG sensing device 206 for a predetermined period of time, for example 20 seconds. Such a control signal can be transmitted to the status generation component 312 for generating a status indicating that no EKG signals have been detected from the operator 202 for more than 20 seconds. Such a status can be used to determine whether the operator 202 has suffered a sudden death or simply is disconnected from the EKG sensing device 206.

The heart rate processing component 308 can be configured to receive heart rate signals generated by the heart rate detection device 208; determine a heart rate of the operator 202, compare the detected heart rate with a threshold heart rate, determine whether the detected heart rate has dropped below the threshold heart rate. In some embodiments, the threshold heart rate retrieved by the heart rate processing device 308 can be personalized. For example, different threshold heart rates may be configured and stored for different operators of the driving apparatus 102. When an operator is identified by the user identification component 304, an appropriate threshold heart rate may be retrieved for the identified operator. In certain embodiments, when it is determined that the heart rate of the operator 202 has dropped below the threshold heart rate, a control signal can be generated to instruct the status generation component 312 to generate a status to indicate such.

The blood level processing component 310 can be configured to receive blood level signal generated by blood level detection device 214; and to analyze the blood level signal. The analysis of the blood level by the blood level processing component 312 can include acquiring the user ID determined by the user identification component 304, retrieving a predetermined normal blood level thresholds for the identified operator 202 using the user ID, comparing the blood level with the retrieved threshold, and/or any other operations. In the case when a blood level is below the threshold, is detected for the identified operator 202, a control signal can be generated to instruct the status generation component 312 to generate a status accordingly.

The status generation component 312 can be configured to generate one or more statuses indicating various abnormal physiological conditions have been detected for operator 202, and/or indicating a sensing device in the driving apparatus has been disconnected from the operator 202. The statuses generated by the status generation component 312 may include a status indicating that below than a threshold level EKG activities have been detected for the operator, a status indicating that below than a threshold heart rate has been detected for the operator, a status indicating that below than a threshold blood level has been detected for the operator, and/or any other statuses. In certain embodiments, the status generated by the status generation component 312 can include a status indicating the EKG sensing device is disconnected from the operator 202, a status indicating EKG signals have not been received for the operator 202 for more than a predetermined period of time.

The communication component 314 can be configured to communicate the status(es) generated by the status generation component 312, identification information regarding the operator 202 and/or driving apparatus 102, and/or any other information to control center 108, and/or any other entities. The communication component 316 can be configured to communicating such information via the network 104.

It should be understood the above-described functionalities attributed to processing 300 can be implemented within the driving apparatus 102. For example, driving apparatus 102 can be equipped with system 300 to process various signals acquired by the sensing devices shown in FIG. 2. However, this is not necessarily the only case. In certain embodiment, part of or the entire functionalities attributed to processing device 300 herein can be implemented at the control center 108. For example, the control center 108 may comprise a server that can be configured to perform part of the operations provided by system 300 as described above.

Figure 4:
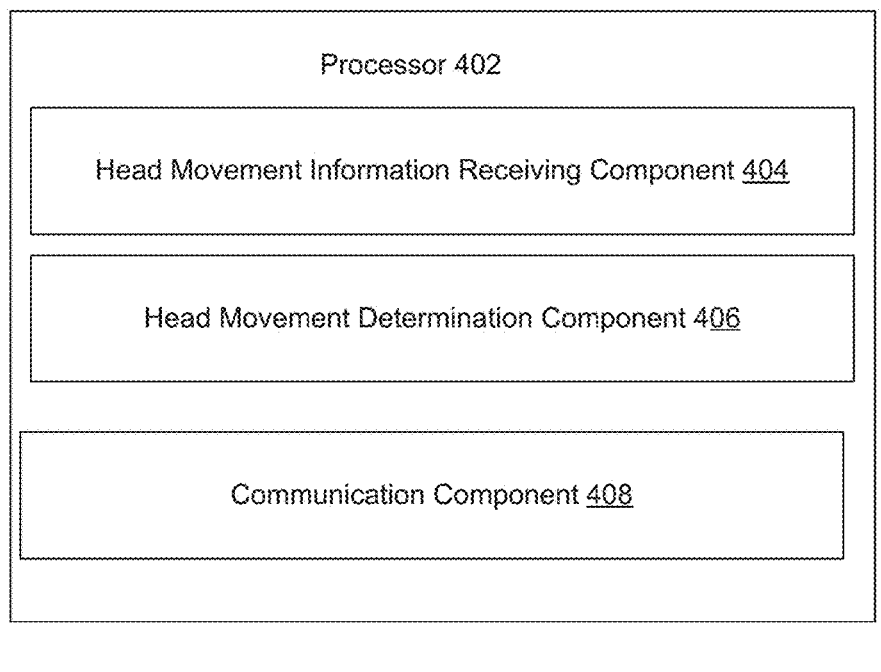
FIG. 4 illustrates an exemplary processing device configured to determine a head movement of the operator of driving apparatus in accordance with the disclosure.
Figure 4:

Attention is now directed to FIG. 4. FIG. 4 illustrates an exemplary processing device 400 configured to determine a head movement of the operator of driving apparatus 102 in accordance with the disclosure. As shown, the processing device 400 can include one or more of a processor 402 configured to implement computer program components. The computer program components can include a head movement information receiving component 404, a head movement determination component 406, a communication component 408 and/or any other components. In some embodiments, the processing device 400 may be arranged within the driving apparatus 102. In those embodiments, the processing device 400 may be configured to communicate with the head movement detection device 214 described herein through short range communication methods, such as Bluetooth, WiFi and/or any short range communication methods. In some embodiments, the processing device 400 may be arranged within the control center 108, for example as a remote server provided by the control center 108. In those embodiments, the processing device 400 may be configured to communicate with the head movement detection device 214 described herein through network 104.

The movement information receiving component 404 may be configured to receive head movement information from the head movement detection device 214. As described above, the head movement information may include images of a head area of the operator 202, or motion data regarding the head of the operator 202 associated with corresponding timestamps. For example, as illustration, an image of a head position of the operator 202 may be received by the head movement information receiving component 404. The image may be associated with a timestamp indicating a time point at which the image was captured for the operator 202. As another illustration, motion data may be received by the head movement information receiving component 404. The motion data may include information indicating a position of a marker attached to the head of the operator at a specific point of time. Other examples are contemplated.

The head movement determination component 406 can be configured to determine a movement of the operator's head based on the head movement information received by the head movement information receiving component 404. Determination of the head movement by the head movement determination component 406 can include determining a direction of movement of the operator's head over a time period. In some embodiments, the head movement determination component 406 can be configured to compare the received head movement information over a time period. In those embodiments, a reference head position may be established by the head movement determination component 406 based on the position of the head movement detection device 214 with respect to the operator 202 in the driver apparatus 102. The direction of the operator's head over a time period can be determined by comparing the head position of the operator at a first time instance in the time period and the head position of the operator at a second time instance in the time period. In some embodiments, the determination of the head movement can include comparing a head position of the driver with the reference head position.

In some embodiments, the head movement determination component 406 can be configured to determine a velocity of the movement of the operator's head over a time period. In some embodiments, the head movement determination component 406 can be configured to determine an orientation change of the head movement over the time period. In some embodiments, the head movement determination component 406 can be configured to determine a movement distance (e.g., an offset) of the operator's head over the time period. Details of these determinations are not provided here since one skilled in the art should understand these determinations involve substantially similar operations described above for determining a direction of the operator's head movement over the time period.

The communication component 406 can be configured to communicate the head movement information with the head movement detection device 214, the head movement determination results with the control center 108, and/or perform any other communications. The communication component 406 can be configured to communicating such information via network 104.

Figure 5:
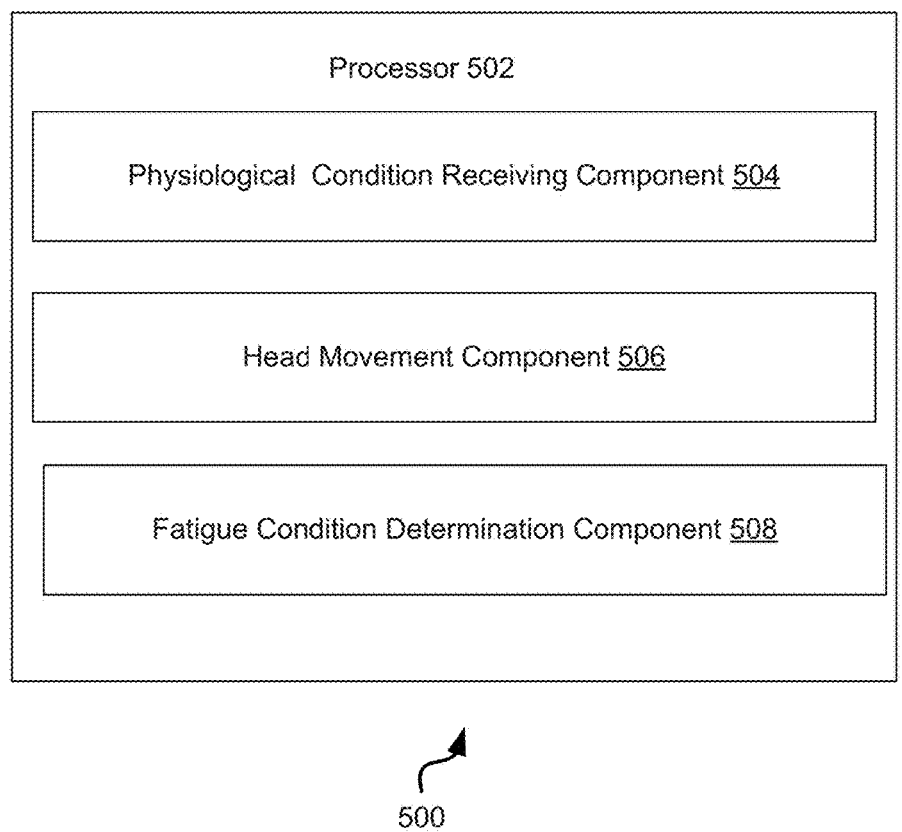
FIG. 5 illustrates an exemplary processing device configured to determine a fatigue condition of an operator of driving apparatus in accordance with the disclosure.

FIG. 5 illustrates an exemplary processing device 500 configured to determine a fatigue condition of an operator of driving apparatus 102 in accordance with the disclosure. As shown, the processing device 500 can include one or more of a processor 502 configured to implement computer program components. The computer program components can include a physiological condition receiving component 502, a head movement component 504, a fatigue condition determination component, and/or any other components. In some embodiments, the processing device 500 may be arranged within the driving apparatus 102. In some embodiments, the processing device 500 may be arranged within the control center 108. In some embodiments, the processing device 500 may be configured to communicate with the processing devices 300 and/or processing device 400. In some embodiments, the processing device 500 may be a part processing device 300 and/or processing device 400.

The physiological condition receiving component 504 can be configured to receive information indicating a physiological condition of the operator 202 is below a predetermined threshold. The physiological condition can include a heart rate, a cardiac activity level, a blood level, and/or any other physiological conditions indicative of the operator 202 might be fatigued. In some embodiments, the physiological condition receiving component 504 can be configured to receive such information from the processing device 300. For example, as illustration, the physiological condition receiving component 504 can be configured to receive status information indicating that the detected heart rate of the operator 202 is below a threshold—e.g., 60 beats per minute. In some embodiments, after receiving such status information, the physiological condition receiving component 504 can be configured to instruct the head movement component 506 to obtain information regarding head movement.

The head movement component 506 can be configured to obtain head movement information regarding the operator 202 within a time window. The head movement information obtained by the head movement component 506 can include a direction, a velocity, a movement distance, an orientation, and/or any other aspects of the head movement of the operator 202. In some embodiments, the head movement component 506 may be configured to obtain such information from the processing device 400. As illustration, the head movement component 506 may be configured to obtain head movement information indicating a direction and a velocity of the head movement of the operator 202 in the last 3 seconds after it is instructed to obtain such information—for example by the physiological condition receiving component 504.

The fatigue condition determination component 508 may be configured to determine occurrence of a fatigue condition of the operator 202 in response to the below than a threshold physiological condition and a downward head movement of the operator 202 being detected. For example, the fatigue condition determination component 508 can be configured to determine the occurrence of the fatigue condition in response to a below than threshold heart rate of the operator 202 having been detected as indicated by the physical receiving component 504; and the head movement of the operator is downward within a very low velocity range (e.g., 0.5-1 degree/second) in the last 3 seconds before the below than threshold heart rate of the operator is detected. In that example, the fatigue condition determination component may generate a fatigue condition detected signal and transmit it to control center 108 to indicate that a fatigue condition is detected for the operator 202 and an appropriate course of action needs to be taken. In some embodiments, the fatigue condition determination component may effectuate a signal, such as a loud audible signal to alert the operator 202 after the fatigue condition is detected.

Figure 6:
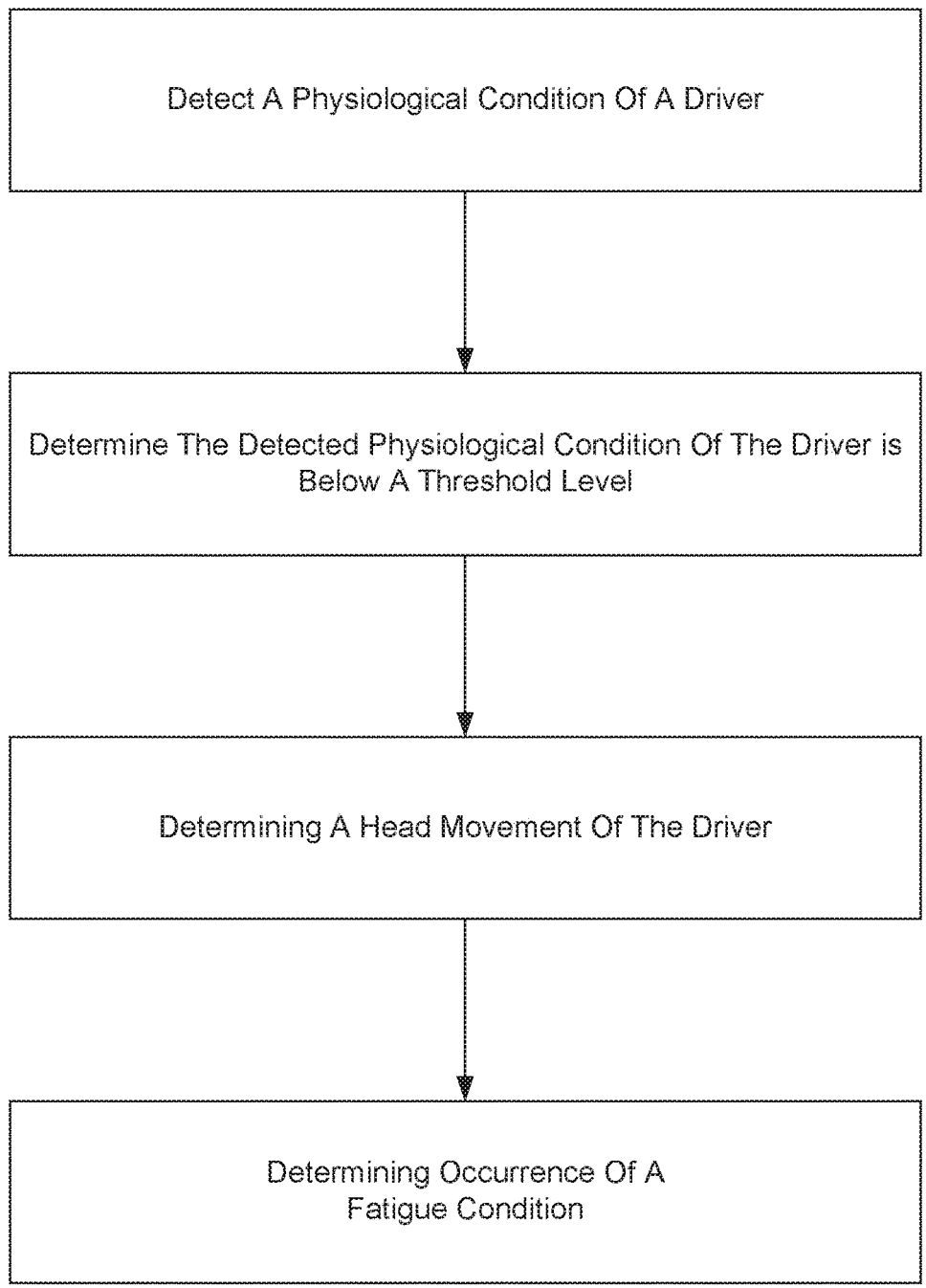
FIG. 6 illustrates one exemplary method for determining a fatigue condition of a driver in accordance with the disclosure.

FIG. 6 illustrates one exemplary method for determining a fatigue condition of a driver in accordance with the disclosure. The operations of method 600 presented below are intended to be illustrative. In some embodiments, method 600 may be accomplished with one or more additional operations not described and/or without one or more of the operations discussed. Additionally, the order in which the operations of method 600 are illustrated in FIG. 6 and described below is not intended to be limiting.

In some embodiments, method 600 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 600 in response to instructions stored electronically on an electronic storage medium. The one or more processing devices may include one or more devices configured through hardware, firmware, and/or software to be specifically designed for execution of one or more of the operations of method 600.

At 602, a signal indicating a physiological condition of the driver can be received. The signals can be received from a sensing device. Examples of such a sensing device are illustrated in FIG. 2. The physiological condition can include EKG activities, a heart rate, a blood level or any other physiological condition of operator. In some implementations, operation 602 can be performed by a EKG signal processing component, a heart rate processing component, a blood level processing component the same as or substantially similar to EKG signal processing component 306, a heart rate processing component 308, a blood level processing component 310 described and illustrated herein.

At 606, the physiological condition as indicated by the signals acquired at 602 can be compared with a predetermined threshold and determined that it has dropped below the predetermined threshold. In some implementations, operation 604 can be performed by a physiological condition receiving component the same as or substantially similar to physiological condition receiving 504 described and illustrated herein.

At 608, information regarding a head movement of the operator within a time window can be obtained in response to the determination the physiological condition of the driver is below the threshold. In some embodiments, the time window may specify an amount of seconds (e.g. 3 seconds) immediately prior to such a determination. In some embodiments, the time window may specify an amount of second immediately after such a determination. In some implementations, operation 608 can be performed by head movement component the same as or substantially similar to status head movement component 506 described and illustrated herein.

At 610, an occurrence of a fatigue condition of the driver can be detected based on the head movement information obtained at 608. In some embodiments, operations at 610 may involve determining a direction, a velocity, a movement distance, an orientation, and/or any other aspects of the head movement of the operator in the time window. For example, as illustration, when the movement direction of the operator's head is determined to be downwards with an average speed between 0.5 to 1 degree per second within the time window (e.g., 3 seconds immediately before the detection of the operator's heart rate has dropped below 60 beats per minute), the occurrence of the fatigue condition can be detected for the operator. In some embodiments, a movement distance of the operator's head within the time window can be determined and can be compared with a threshold distance when determining whether the fatigue condition has occurred. For example, the head movement of the operator has breached the threshold distance within the time window, it can be determined that the fatigue condition has occurred. In some implementations, operation 610 can be performed by a fatigue condition determination component the same as or substantially similar to fatigue condition determination component 508 described and illustrated herein.

Figure 7:
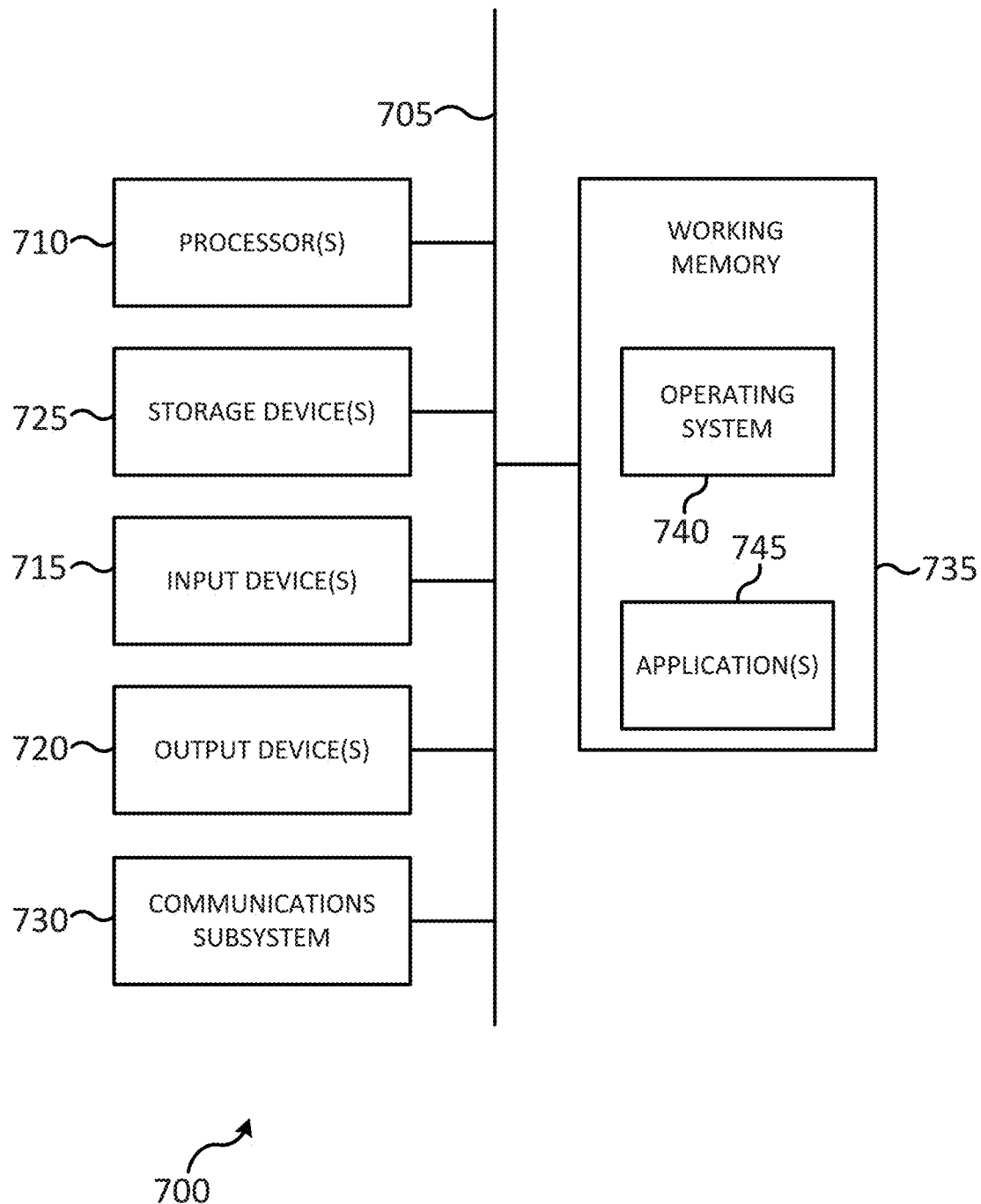
FIG. 7 illustrates a simplified computer system, according to an exemplary embodiment of the present disclosure

FIG. 7 illustrates a simplified computer system, according to an exemplary embodiment of the present disclosure. A computer system 700 as illustrated in FIG. 7 may be incorporated into devices such as a portable electronic device, mobile phone, or other device as described herein. FIG. 7 provides a schematic illustration of one embodiment of a computer system 700 that can perform some or all of the steps of the methods provided by various embodiments. It should be noted that FIG. 7 is meant only to provide a generalized illustration of various components, any or all of which may be utilized as appropriate. FIG. 7, therefore, broadly illustrates how individual system elements may be implemented in a relatively separated or relatively more integrated manner.

The computer system 700 is shown comprising hardware elements that can be electrically coupled via a bus 705, or may otherwise be in communication, as appropriate. The hardware elements may include one or more processors 710, including without limitation one or more general-purpose processors and/or one or more special-purpose processors such as digital signal processing chips, graphics acceleration processors, and/or the like; one or more input devices 715, which can include without limitation a mouse, a keyboard, a camera, and/or the like; and one or more output devices 720, which can include without limitation a display device, a printer, and/or the like.

The computer system 700 may further include and/or be in communication with one or more non-transitory storage devices 725, which can comprise, without limitation, local and/or network accessible storage, and/or can include, without limitation, a disk drive, a drive array, an optical storage device, a solid-state storage device, such as a random access memory ("RAM"), and/or a read-only memory ("ROM"), which can be programmable, flash-updateable, and/or the like. Such storage devices may be configured to implement any appropriate data stores, including without limitation, various file systems, database structures, and/or the like.

The computer system 700 might also include a communications subsystem 730, which can include without limitation a modem, a network card (wireless or wired), an infrared communication device, a wireless communication device, and/or a chipset such as a Bluetooth™ device, an 802.11 device, a WiFi device, a WiMax device, cellular communication facilities, etc., and/or the like. The communications subsystem 730 may include one or more input and/or output communication interfaces to permit data to be exchanged with a network such as the network described below to name one example, other computer systems, television, and/or any other devices described herein. Depending on the desired functionality and/or other implementation concerns, a portable electronic device or similar device may communicate image and/or other information via the communications subsystem 730. In other embodiments, a portable electronic device, e.g. the first electronic device, may be incorporated into the computer system 700, e.g., an electronic device as an input device 715. In some embodiments, the computer system 700 will further comprise a working memory 735, which can include a RAM or ROM device, as described above.

The computer system 700 also can include software elements, shown as being currently located within the working memory 735, including an operating system 740, device drivers, executable libraries, and/or other code, such as one or more application programs 745, which may comprise computer programs provided by various embodiments, and/or may be designed to implement methods, and/or configure systems, provided by other embodiments, as described herein. Merely by way of example, one or more procedures described with respect to the methods discussed above, such as those described in relation to FIG. 7, might be implemented as code and/or instructions executable by a computer and/or a processor within a computer; in an aspect, then, such code and/or instructions can be used to configure and/or adapt a general purpose computer or other device to perform one or more operations in accordance with the described methods.

A set of these instructions and/or code may be stored on a non-transitory computer-readable storage medium, such as the storage device(s) 725 described above. In some cases, the storage medium might be incorporated within a computer system, such as computer system 700. In other embodiments, the storage medium might be separate from a computer system e.g., a removable medium, such as a compact disc, and/or provided in an installation package, such that the storage medium can be used to program, configure, and/or adapt a general purpose computer with the instructions/code stored thereon. These instructions might take the form of executable code, which is executable by the computer system 700 and/or might take the form of source and/or installable code, which, upon compilation and/or installation on the computer system 700 e.g., using any of a variety of generally available compilers, installation programs, compression/decompression utilities, etc., then takes the form of executable code.

It will be apparent to those skilled in the art that substantial variations may be made in accordance with specific requirements. For example, customized hardware might also be used, and/or particular elements might be implemented in hardware, software including portable software, such as applets, etc., or both. Further, connection to other computing devices such as network input/output devices may be employed.

As mentioned above, in one aspect, some embodiments may employ a computer system such as the computer system 700 to perform methods in accordance with various embodiments of the technology. According to a set of embodiments, some or all of the procedures of such methods are performed by the computer system 700 in response to processor 710 executing one or more sequences of one or more instructions, which might be incorporated into the operating system 740 and/or other code, such as an application program 745, contained in the working memory 735. Such instructions may be read into the working memory 735 from another computer-readable medium, such as one or more of the storage device(s) 725. Merely by way of example, execution of the sequences of instructions contained in the working memory 735 might cause the processor(s) 710 to perform one or more procedures of the methods described herein. Additionally or alternatively, portions of the methods described herein may be executed through specialized hardware.

The terms "machine-readable medium" and "computer-readable medium," as used herein, refer to any medium that participates in providing data that causes a machine to operate in a specific fashion. In an embodiment implemented using the computer system 700, various computer-readable media might be involved in providing instructions/code to processor(s) 710 for execution and/or might be used to store and/or carry such instructions/code. In many implementations, a computer-readable medium is a physical and/or tangible storage medium. Such a medium may take the form of a non-volatile media or volatile media. Non-volatile media include, for example, optical and/or magnetic disks, such as the storage device(s) 725. Volatile media include, without limitation, dynamic memory, such as the working memory 735.

Common forms of physical and/or tangible computer-readable media include, for example, a floppy disk, a flexible disk, hard disk, magnetic tape, or any other magnetic medium, a CD-ROM, any other optical medium, punchcards, papertape, any other physical medium with patterns of holes, a RAM, a PROM, EPROM, a FLASH-EPROM, any other memory chip or cartridge, or any other medium from which a computer can read instructions and/or code.

Various forms of computer-readable media may be involved in carrying one or more sequences of one or more instructions to the processor(s) 710 for execution. Merely by way of example, the instructions may initially be carried on a magnetic disk and/or optical disc of a remote computer. A remote computer might load the instructions into its dynamic memory and send the instructions as signals over a transmission medium to be received and/or executed by the computer system 700.

The communications subsystem 730 and/or components thereof generally will receive signals, and the bus 705 then might carry the signals and/or the data, instructions, etc. carried by the signals to the working memory 735, from which the processor(s) 710 retrieves and executes the instructions. The instructions received by the working memory 735 may optionally be stored on a non-transitory storage device 725 either before or after execution by the processor(s) 710.

The methods, systems, and devices discussed above are examples. Various configurations may omit, substitute, or add various procedures or components as appropriate. For instance, in alternative configurations, the methods may be performed in an order different from that described, and/or various stages may be added, omitted, and/or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Specific details are given in the description to provide a thorough understanding of exemplary configurations including implementations. However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the spirit or scope of the disclosure.

Also, configurations may be described as a process which is depicted as a schematic flowchart or block diagram. Although each may describe the operations as a sequential process, many of the operations can be performed in parallel or concurrently. In addition, the order of the operations may be rearranged. A process may have additional steps not included in the figure. Furthermore, examples of the methods may be implemented by hardware, software, firmware, middleware, microcode, hardware description languages, or any combination thereof. When implemented in software, firmware, middleware, or microcode, the program code or code segments to perform the necessary tasks may be stored in a non-transitory computer-readable medium such as a storage medium. Processors may perform the described tasks.

Having described several example configurations, various modifications, alternative constructions, and equivalents may be used without departing from the spirit of the disclosure. For example, the above elements may be components of a larger system, wherein other rules may take precedence over or otherwise modify the application of the technology. Also, a number of steps may be undertaken before, during, or after the above elements are considered. Accordingly, the above description does not bind the scope of the claims.

As used herein and in the appended claims, the singular forms "a", "an", and "the" include plural references unless the context clearly dictates otherwise. Thus, for example, reference to "a user" includes a plurality of such users, and reference to "the processor" includes reference to one or more processors and equivalents thereof known to those skilled in the art, and so forth.

Also, the words "comprise", "comprising", "contains", "containing", "include", "including", and "includes", when used in this specification and in the following claims, are intended to specify the presence of stated features, integers, components, or steps, but they do not preclude the presence or addition of one or more other features, integers, components, steps, acts, or groups.

What is claimed is:

1. A method for detecting occurrence a fatigue condition of an operator of a driving apparatus, the method being implemented in a processor configured to execute machine-readable instructions, the method comprising:
   receiving a signal indicating a physiological condition of the operator;
   determining the physiological condition of the operator is below a threshold;
   in response to determining the physiological condition of the operator is below the threshold, obtaining head movement information regarding a movement of the operator's head within a time window, wherein the time window specifies an amount of seconds immediately prior to the determination that the operator's physiological condition is below the threshold;
   determining the head movement information indicates that operator's head is moving downwards within the time window; and
   in response to the head movement information indicating the operator's head is moving downwards within the time window and further to the physiological condition of the operator is below the threshold, generating a signal indicating a fatigue condition is detected for the operator.

2. The method of claim 1, wherein the physiological condition of the operator includes a heart rate, a cardiac activity level or a blood level of the operator.

3. The method of claim 1, wherein determining the head movement information indicates that operator's head is moving downwards within the time window includes:
   determining an average velocity of the head movement of the operator's head in the time window; and
   determining the average velocity of the head movement of the operator's head in the time window is within a predetermined velocity range.

4. The method of claim 1, wherein determining the head movement information indicates that operator's head is moving downwards within the time window includes:
   determining a movement distance of the operator's head has breached a threshold distance within the time window.

5. The method of claim 1, wherein determining the head movement information indicates that operator's head is moving downwards within the time window includes:
   determining an orientation change of the operator's head in the time window.

6. The method of claim 1, wherein the time window specifies an amount of seconds immediately after the determination that the operator's physiological condition is below the threshold.

7. The method of claim 1, wherein the driving apparatus includes a vehicle, a train, a ship, or an airplane.

8. The method of claim 1, further comprising: effectuating a loud audible signal to alert the operator after the fatigue condition is detected for the operator.

9. A system for detecting occurrence a fatigue condition of an operator of a driving apparatus, the system comprising one or more processors configured to execute machine-readable instructions, wherein when the machine-readable instructions are executed, the one or more processors are caused to perform:
   receiving a signal indicating a physiological condition of the operator;

determining the physiological condition of the operator is below a threshold;

in response to determining the physiological condition of the operator is below the threshold, obtaining head movement information regarding a movement of the operator's head within a time window, wherein the time window specifies an amount of seconds immediately prior to the determination that the operator's physiological condition is below the threshold;

determining the head movement information indicates that operator's head is moving downwards within the time window; and in response to the head movement information indicating the operator's head is moving downwards within the time window and further to the physiological condition of the operator is below the threshold, generating a signal indicating a fatigue condition is detected for the operator.

10. The system of claim 9, wherein the physiological condition of the operator includes a heart rate, a cardiac activity level or a blood level of the operator.

11. The system of claim 9, wherein determining the head movement information indicates that operator's head is moving downwards within the time window includes:

determining an average velocity of the head movement of the operator's head in the time window; and determining the average velocity of the head movement of the operator's head in the time window is within a predetermined velocity range.

12. The system of claim 9, wherein determining the head movement information indicates that operator's head is moving downwards within the time window includes:

determining a movement distance of the operator's head has breached a threshold distance within the time window.

13. The system of claim 9, wherein determining the head movement information indicates that operator's head is moving downwards within the time window includes:

determining an orientation change of the operator's head in the time window.

14. The system of claim 9, wherein the time window specifies an amount of seconds immediately after the determination that the operator's physiological condition is below the threshold.

15. The system of claim 9, wherein the driving apparatus includes a vehicle, a train, a ship, or an airplane.

16. The system of claim 9, wherein the one or more processors are further caused to perform effectuating a loud audible signal to alert the operator after the fatigue condition is detected for the operator.

* * * * *